(12) United States Patent
Kojima et al.

(10) Patent No.: US 6,905,825 B2
(45) Date of Patent: Jun. 14, 2005

(54) METHOD FOR ISOLATING AND PURIFYING NUCLEIC ACIDS

(75) Inventors: Kyoko Kojima, Hino (JP); Satoshi Ozawa, Musashino (JP)

(73) Assignee: Hitachi, Ltd., Tokyo (JP)

( * ) Notice: Subject to any disclaimer, the term of this patent is extended or adjusted under 35 U.S.C. 154(b) by 177 days.

(21) Appl. No.: 10/020,906

(22) Filed: Dec. 19, 2001

(65) Prior Publication Data

US 2002/0192667 A1 Dec. 19, 2002

(30) Foreign Application Priority Data

Jun. 5, 2001 (JP) .................................. 2001-169566

(51) Int. Cl.[7] .......................... C12Q 1/68; C12N 15/00; C12N 15/63; C12N 1/20; C07H 21/04
(52) U.S. Cl. ...................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2; 536/24.3; 935/6; 436/518

(56) References Cited

U.S. PATENT DOCUMENTS

| | | | | |
|---|---|---|---|---|
| 5,153,319 A | * | 10/1992 | Caruthers | .................. 536/27 |
| 5,910,423 A | * | 6/1999 | Yamazaki | .................. 435/28 |
| 6,211,349 B1 | * | 4/2001 | Dale | .................. 536/23.1 |
| 6,368,400 B1 | * | 4/2002 | Baldwin | .................. 106/481 |

FOREIGN PATENT DOCUMENTS

| | | |
|---|---|---|
| JP | 6-205676 | 12/1992 |
| JP | 8-501321 | 6/1994 |
| JP | 9-20793 | 7/1995 |
| JP | 9-327290 | 6/1996 |
| JP | 9-327291 | 6/1996 |
| JP | 11-127854 | 10/1997 |
| JP | 11-127-854 | 10/1997 |
| JP | 11-169170 | 12/1997 |
| JP | 11-266864 | 3/1998 |
| WO | WO 95/01359 | 7/1993 |

OTHER PUBLICATIONS

Stratagene Catalog, "Gene Characterization kits", p. 39, 1988.*
Webster's II New Riverside University Dictionary, pp. 69, 80, 1984.*
Bert Vogelstein and David Gillespie, "Preparative and Analytical Purification of DNA from Agarose", Proc. Natl. Acad. Sci., Vol 76, No 2, Feb. 1979, pp. 615–619.
R. Boom, C.J.A. Sol, M.M.M. Salimans, C.L. Jansen, P.M.E. Wertheim–Van Dillen, and J. Van Der Noordaa, "Rapid and Simple Method for Purification of Nucleic Acids", Journal of Clinical Microbiology, Mar. 1990, vol. 28, No. 3, pp. 495–503.
Toshio Ohshima, Hayato Miyachi, Atsuko Masukawa, Hisae Fusegawa and Yasuhiko Ando, Usefulness of the Positive Internal Control for Detection of Mycobacterium Tuberculosis in a Fully Automated PCR Analyzer COBAS® AMPLICOA™, JJCLA vol. 22, No. 2, 1997, pp. 145–150.
Organic Composite Chemical Society "Solvents", 1st print Nov. 20, 1997.
John A. Riddick, William B. Bunger and Theodore K. Sakano; "Organic Solvents", Techniques of Chemistry, vol. II, pp. 67, 193, 299, 301.

* cited by examiner

*Primary Examiner*—Jeffrey Fredman
*Assistant Examiner*—Arun Chakrabarti
(74) *Attorney, Agent, or Firm*—Reed Smith LLP; Stanley P. Fisher, Esq.; Juan Carlos A. Marquez, Esq.

(57) ABSTRACT

A method for isolating and purifying nucleic acids with an improved recovery yield is provided. A mixed solution containing the nucleic acids, salts, and an organic solvent is contacted with an adsorption support to cause the nucleic acids to be adsorbed on the support. Then, the nucleic acids are desorbed from the support using an elution buffer. At least one compound containing 2 to 10 carbon atoms as selected from the group consisting of aliphatic ether, aliphatic ester, and aliphatic ketone is used as the organic solvent. The method improves the yield of nucleic acids collection, is easy to implement and less susceptible to contamination.

9 Claims, 9 Drawing Sheets

METHOD FOR ISOLATING AND PURIFYING NUCLEIC ACIDS

BACKGROUND OF THE INVENTION

1. Field of the Invention

The present invention relates to a method for isolating and purifying nucleic acids by eluting nucleic acids from nucleic acid-containing samples, such as biological materials.

2. Description of Related Art

An efficient method known in the art for isolating and purifying nucleic acids is based on the adsorption of the nucleic acids on glass or silica particles in the presence of a chaotropic salt, followed by recovering the nucleic acids (Vogelstein, B. and Gillespie, D. (1979); "Preparative and analytical purification of DNA from agarose", Proc. Natl. Acad. Sci. USA 76: 615–619). According to this method and using high concentrations of a chaotropic salt, such as sodium iodide, sodium perchlorate or guanidine thiocyanate, DNA can be isolated and purified from agarose, or RNA or DNA can be isolated and purified from various mixtures (Boom, R. (1990); Rapid and simple method for purification of nucleic acids, J. Clin. Microbiol. 28: 495–503).

Nucleic acids after purification are often subjected to the polymerase chain reaction (PCR). The technique of PCR amplifies nucleic acids in a sequence-specific manner and therefore is widely used in genetic or DNA diagnosis. In utilizing this PCR technique routinely for clinical purposes, several problems arise. It is known, among others, that inhibitor substances remaining un-removed in the nucleic acids purification step inhibit the PCR. Such inhibitor substances include hemoglobin and surfactants used in the nucleic acids extraction process, for instance. With such a background, it is pointed out that the processes for extracting and purifying nucleic acids are important (Oshima et al., JJCL A, 22(2), 145–150 (1997)).

The procedures in the extracting process which have so far been carried out manually are complicated and requires skills. As such, automation by instruments is desired. Thus, it is demanded that an extraction method suitable for automation be developed, inclusive of reagents to be used. There is a nucleic acids extraction method suitable for automation described in JP-A-127854/1999, and another method using the apparatus described in JP-A-266864/1999. Further, there are reagents allegedly suitable for nucleic acids extraction on an automated apparatus described in Tokuhyo (Japanese Translation of Unexamined PCT Appln.) No. 501321/1996. According to the method using the reagents described in the Tokuhyo No. 501321/1996, the nucleic acids to be isolated and purified from a solution containing a high concentration (ionic strength) of salts and a high concentration of alcohol are brought into contact with an adsorption support within a column for genome extraction so as to adsorb them on the support then desorb them from the adsorption support by means of a solution containing lower concentration (ionic strength) of salts.

However, the method for isolating and purifying nucleic acids using the reagents described in the Tokuhyo No. 501321/1996 has a problem in that the yield of nucleic acids collection is low. The method, which uses the column for genome extraction described in JP-A-127854/1999, requires a long period of time for contacting the nucleic acids with the adsorption support to adsorb them thereon, since the viscosity of the solution is high.

SUMMARY OF THE INVENTION

It is an object of the present invention to provide a method for isolating and purifying nucleic acids by which the recovery yield is improved and the time required for the nucleic acids recovery is reduced such that the method is excellent in operability and is less susceptible to contamination.

The method for isolating and purifying nucleic acids as provided by the present invention comprises allowing nucleic acids to be adsorbed on an inorganic or organic support from a mixed solution comprising a nucleic acid-containing sample, high concentration of salts and an organic solvent, and then desorbing the nucleic acids from the support with an elution buffer consisting of an aqueous solution. The support is washed with a washing buffer prior to recovery to remove components other than the nucleic acids. The nucleic acids are, for example, derived from whole blood.

Chaotropic salts may be used as the salts. In particular, guanidine hydrochloride, guanidine thiocyanate or potassium iodide are used within the concentration range of 1 M to 8 M.

The organic solvent (organic compound) comprises at least one compound containing 2 to 10 carbon atoms selected from the group consisting of aliphatic ethers, aliphatic esters, and aliphatic ketones. The concentration of the organic solvents in the mixed solution is 5% to 50% by volume.

As typical example of the aliphatic ether, which can be used as the organic solvent (organic compound) in the mixed solution, includes at least one of ethylene glycol dimethyl ether, ethylene glycol diethyl ether, propylene glycol dimethyl ether, propylene glycol diethyl ether, diethylene glycol dimethyl ether, diethylene glycol diethyl ether, tetrahydrofuran, and 1,4-dioxane.

As typical example of the aliphatic ester used as the organic solvent (organic compound) in the mixed solution comprises at least one of propylene glycol monomethyl ether acetate, and ethyl lactate.

As typical example of the aliphatic ketone used as the organic solvent (organic compound) in the mixed solution comprises at least one of hydroxyacetone, acetone, and methyl ethyl ketone.

In applying the present invention, it is recommended that the mixed solution contains 0.1% to 50% by volume of a surfactant and 0.1% to 5% by weight of a defoaming agent.

As the inorganic support, a porous or nonporous material consisting of silica, alumina, zeolite, titanium dioxide and/or the like is used.

The washing buffer contains a high concentration of organic solvents such as alcohols, and serves to remove components other than the nucleic acids by repeating a separation procedure of sucking or centrifugation a number of times.

According to the method for isolating and purifying nucleic acids in accordance with the present invention, the obtained nucleic acid-containing solution shows a reduced viscosity, the formation of bubbles can be controlled, and defoaming is promoted, hence the operability is improved. The yield of nucleic acids recovered or collected also increases without incurring move contamination. Additionally, the nucleic acids recovery time is shortened.

Other and further objects, features and advantages of the invention will appear more fully from the following description.

BRIEF DESCRIPTION OF THE DRAWINGS

The preferred embodiments of the present invention are illustrated in the accompanying drawings in which.

DETAILED DESCRIPTION OF THE PREFERRED EMBODIMENTS

Figure 1:
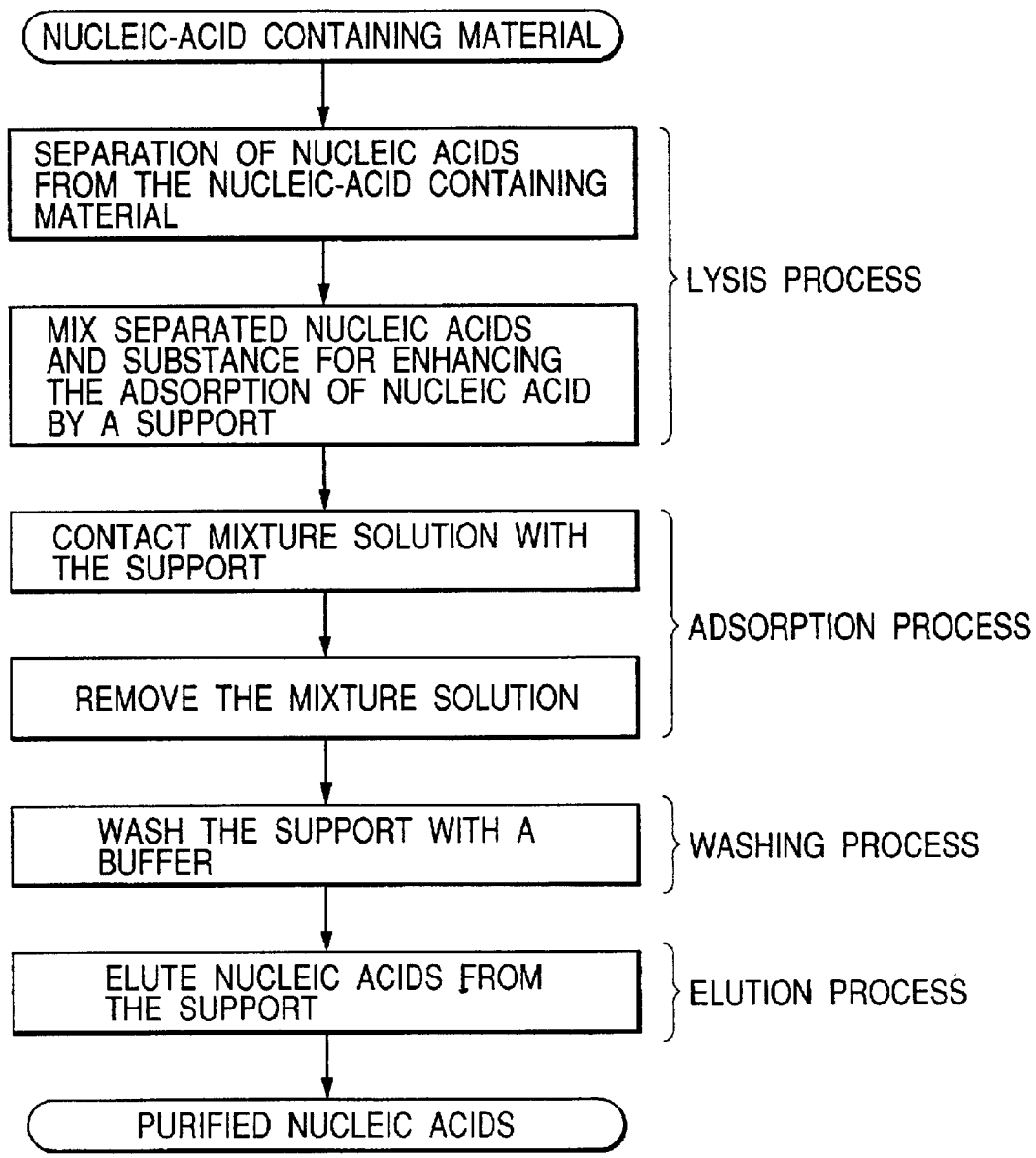
FIG. 1 shows the nucleic acids extraction process in one embodiment of the present invention.

According to the present invention, the isolation and purification of the nucleic acids from an organism, i.e. DNAs, may be carried out based on the method illustrated in FIG. 1. FIG. 1 shows the main elements in the processes, described in JP-A-127854/1999. Following explain the details of each process.

Figure 2:
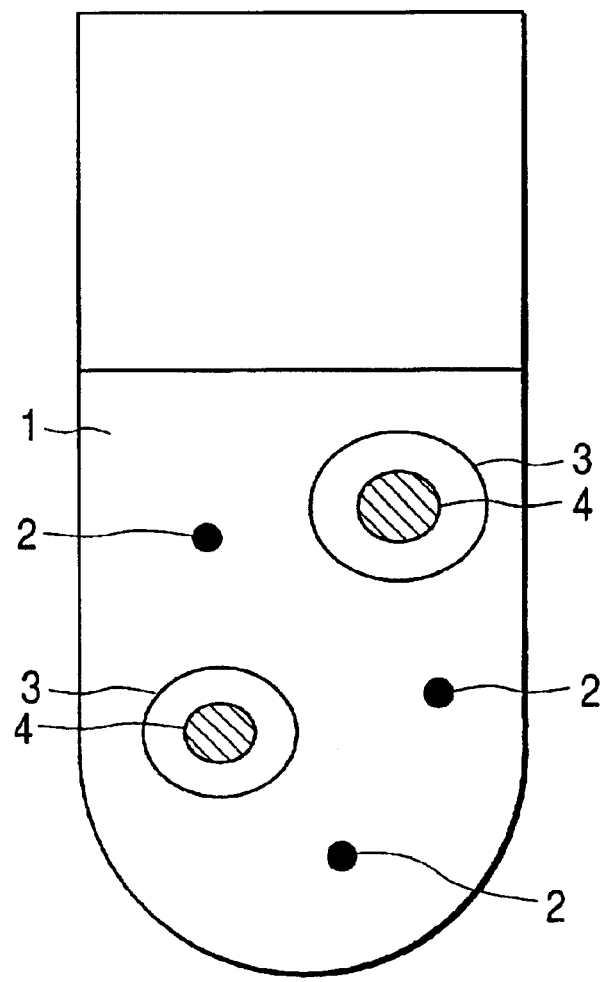
FIG. 2 shows the constitution of whole blood in the embodiments of the invention.

FIGS. 2 to 5 illustrate the processes for extracting the nucleic acids from whole blood using the nucleic acids extraction reagents according to the processes described in FIG. 1. In the following description, nucleic acids extraction from 100 $\mu$L of human whole blood is taken as an example. As shown in FIG. 2, human whole blood 1 contains erythrocytes 2, leukocytes 3, and other components. Nucleic acids are mainly derived from the nucleus 4 of the leukocyte 3.

Figure 3:
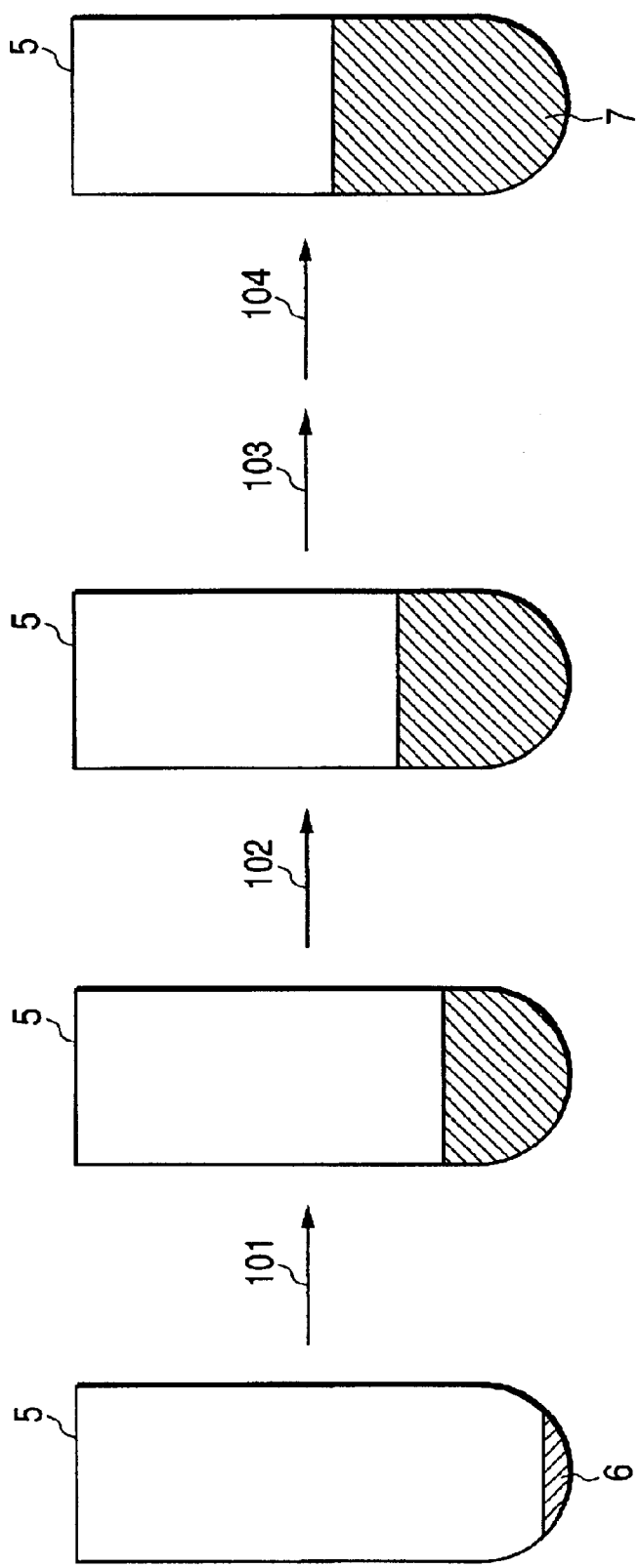
FIG. 3 shows the lysis process for nucleic extracting the acids from the whole blood in FIG. 2.

As shown in FIG. 3, 10 $\mu$L of proteinase K (6) is added to a tube 5. Then, 100 $\mu$L of whole blood 1 is added to the tube 5. This step is indicated by 101. Then, 100 $\mu$L of a lysis buffer is added, and the resulted mixture is stirred. This step is indicated by 102. This lysis buffer contains 1 M to 8 M of a chaotropic salt and a surfactant at not more than 50% by volume. The solution in the tube 5 is incubated at 56° C. for 10 minutes, whereby the leukocytes 3 are decomposed, and the nucleic acids within the nucleus come out therefrom into the solution. This step is indicated by 103. Thereafter, 100 $\mu$L of an additive solution (e.g. organic solvent such as EGDEE (ethylene glycol diethyl ether) or Diglyme (diethylene glycol dimethyl ether)) is added, then the whole mixture is stirred to provide a mixed solution 7. This step is indicated by 104. The procedure until the step 104 is referred to as a "lysis process".

After this lysis process, there are several methods available for recovering or collecting the nucleic acids. Each method comprises an adsorption process, a washing process, and an elution process. As typical examples, there are a spin column method and a bi-directional method.

Figure 4:
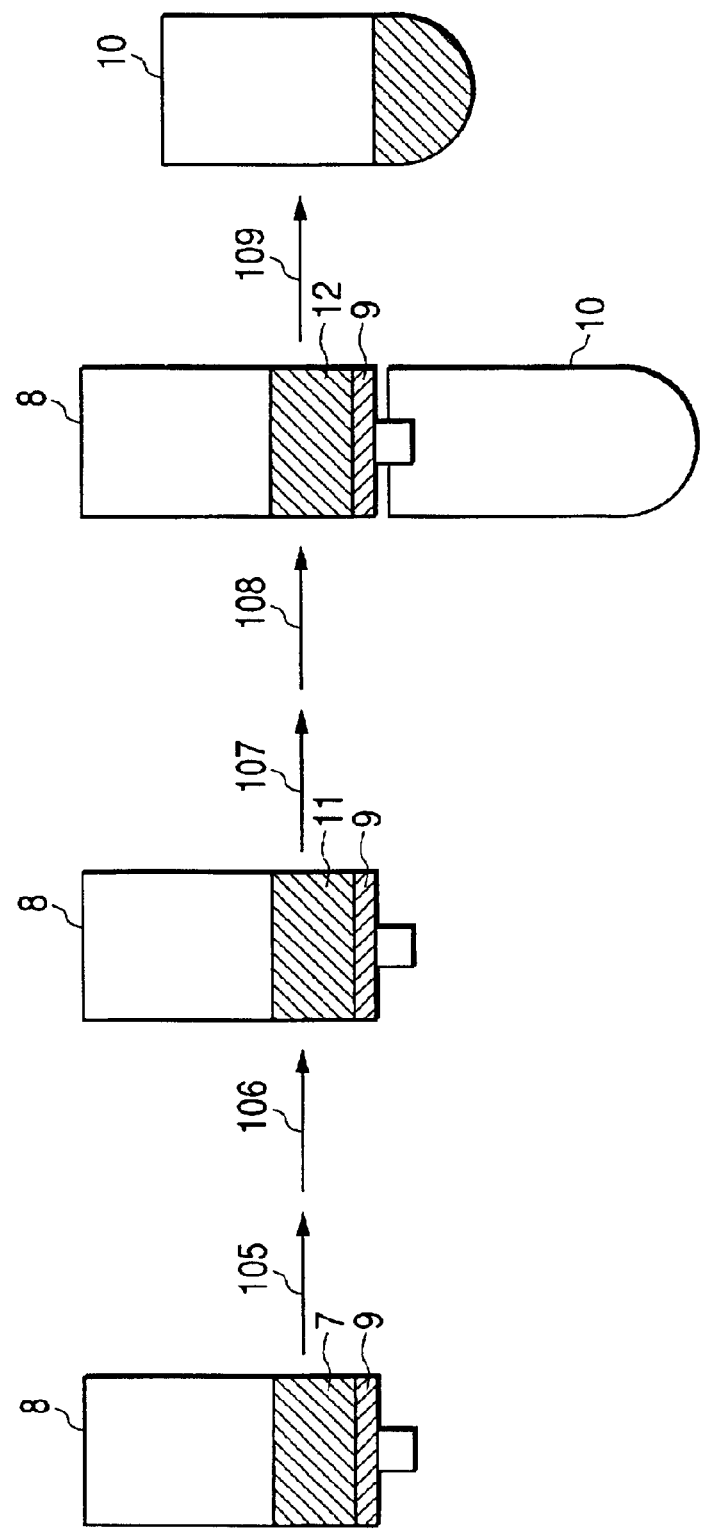
FIG. 4 shows the procedure (first method) for extracting the nucleic acids from the whole blood in the first embodiment of the invention.

FIG. 4 illustrates how the spin column method (hereinafter referred to as "first method") is applied in the invention. After the additive solution is added, the mixed solution 7 is transferred from the tube 5 to a spin column 8. The inside of the bottom portion of the spin column 8 is packed with an adsorption support 9 made of very fine silica or glass wool in a filter paper-like form. Alternatively, the support is made of organic hybrid materials. The mixed solution 7 containing the additive solution is passed through the adsorption support 9 by a sucking force to cause the nucleic acids to be adsorbed on the adsorption support 9 (adsorption process). This process is indicated by 105. Thereafter, 500 $\mu$L of a washing buffer 11 containing 20% to 80% of an organic solvent, such as an alcohol, is poured into the spin column 8. This step is indicated by 106. Then, the adsorption support 9 is washed by a sucking force to remove other components than the nucleic acids. This is step 107 (washing process). This washing process is repeated twice, but the nucleic acids adsorbed are not desorbed. Thereafter, a low salt concentration elution buffer 12 is added, then the mixture is allowed to stand for 2 minutes to 5 minutes. This step is indicated by 108. The nucleic acids are eluted from the adsorption support 9 and finally recovered/collected in a tube 10 by a sucking force (step 109) (elution process). A typical elution buffer has the following composition: 50 mmol Tris/HCl (pH 8.5) and 0.1 mmol EDTA•2Na. In the first method, a centrifugation procedure can be employed in each step for simple and rapid treatment.

Figure 5:
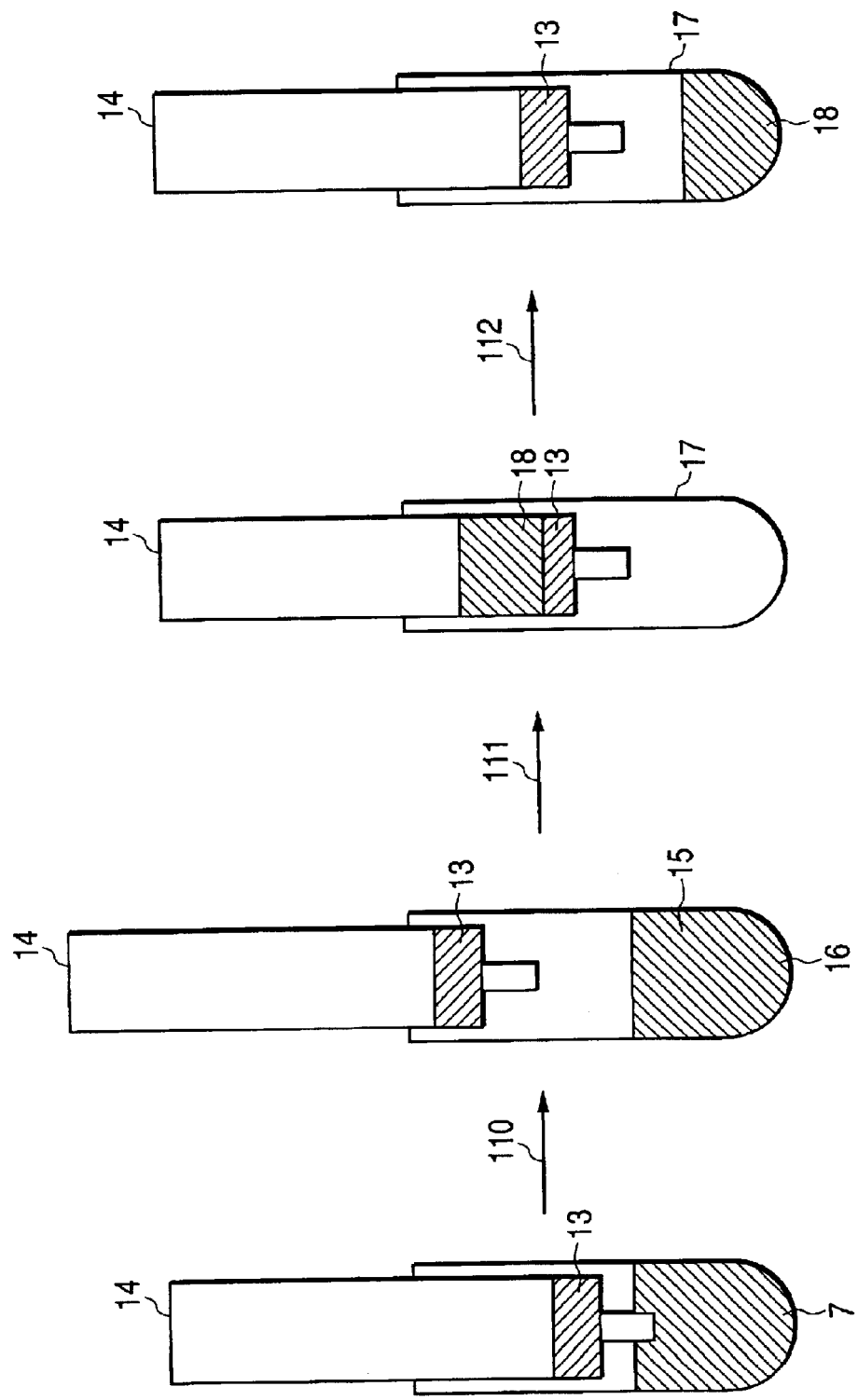
FIG. 5 shows the procedure (second method) for extracting the nucleic acids from the whole blood in the second embodiment of the invention.

FIG. 5 illustrates how the bi-directional method (hereinafter referred to as "second method") is applied in the invention. In this second embodiment of the invention, a cylindrical hollow column 14 is used, which has an adsorption support 13 of a lower density of glass or quartz wool or the like than the one in the first embodiment. In this column 14, the mixed solution 7 (after adding the additive solution) is passed through the support 13 (bi-directionally) a plurality of times (suction and discharge) to enhance the nucleic acids to be adsorbed on the adsorption support 13. This is step 110 (adsorption process). Then another tube 16 containing 500 $\mu$L of a washing buffer 15 (containing an organic solvent, such as an alcohol), is used to remove other components than the nucleic acids. This washing process is carried out at least twice. Thereafter, an elution buffer 18 (100 $\mu$L) placed in a tube 17 and heated in advance to 70° C. is sucked up to a level such that it comes into contact with the adsorption support 13 within the column 14. The elution buffer is allowed to stand in that condition for about 2 minutes. This process is indicated by 111. By this procedure, the nucleic acids are eluted from the adsorption support 13 into the elution buffer 18. The elution buffer (eluate) 18 is discharged into the tube 17, and the nucleic acids are collected. This process is indicated by 112. A typical elution buffer has the following composition: 50 mmol Tris/HCl (pH 8.5) and 0.1 mmol EDTA•Na.

The materials, reagents and samples mentioned above are described below in detail.

1. Materials for nucleic acids adsorption and columns 1.1 Spin column

Three layers of Whatman glass fiber filter paper, for instance, are fixed on a column for centrifugal chromatography (spin column). The column is used according to the first method as shown in FIG. 4.

1.2 Column for nucleic acids adsorption

A column has a support made form the same quartz wool with a diameter of 0.5 μm to 30 μm of a lower density than the support in the first method (product of Tosoh Quartz Corp. or Toshiba Ceramics Co., Ltd., and used for nucleic acids adsorption in JP-A-266864/1999). This is used according to the second method shown in FIG. 5.

2. Nucleic acid-containing samples 2.1 Blood (human)

Blood just collected or frozen at −20° C. is used.

2.2 Tissues

Fresh or frozen tissues are used.

2.3 Plant

A plant mashed in a mortar is used fresh or frozen in liquid nitrogen.

2.4 Cells

Isolated cells or isolated/incubated cells are fresh or in a frozen state.

3. Reagents 3.1 Lysis buffers

Each lysis buffer comprises chaotropic salts, a surfactants, a defoaming agent, and another salt components, as follow.

3.1.1 Chaotropic salts

One of the following is used as the chaotropic salt.

KI: Potassium iodide

GuHCl: Guanidine hydrochloride

GuHSCN: Guanidine thiocyanate 3.1.2 Surfactants

One of the following is used as the surfactant.

Tween 20: Polyoxyethylene(20)sorbitan monolaurate

Tween 40: Polyoxyethylene(20)sorbitan monopalmitate

Tween 60: Polyoxyethylene(20)sorbitan monostearate

Tween 80: Polyoxyethylene(20)sorbitan monooleate

Tween 85: Polyoxyethylene(20)sorbitan trioleate

Triton X-100: Polyoxyethylne(10) isooctylphenyl ether

Defoaming agent

CE-457: Disfoam, defoaming agent produced by NOFCO (NOF Corp.), a polyalkylene glycol derivative 3.1.4 Other salts EDTA•2Na: Ethylenediaminetetraacetic acid disodium salt Tris: Tris(hydroxymethyl)aminomethane 3.2 Additive solutions One of the following organic solvents is used as the additive solution.

EGDME: Ethylene glycol dimethyl ether

EGDEE: Ethylene glycol diethyl ether

PGDME: Propylene glycol dimethyl ether

PGDEE: Propylene glycol diethyl ether

DIGLYME: Diethylene glycol dimethyl ether

DGDEE: Diethylene glycol diethyl ether

THF: Tetrahydrofuran

DX: 1,4-Dioxane

PGMEA: Propylene glycol monomethyl ether acetate

EL: Ethyl lactate

HAC: Hydroxyacetone

AC: Acetone

MEK: Methyl ethyl ketone 3.3 Washing buffers

One of the following compositions is used as the washing buffer.

W1: 25 mmol/l potassium acetate, 70 volume % ethanol

W2: 25 mmol/l potassium acetate, 50 volume % ethanol

W3: 25 mmol/l Tris/HCl, 50 volume % ethanol

W4: 10 mmol/l Tris/HCl (pH 5), 0.1 mmol/l EDTA•2Na, 50 volume % ethanol 3.4 Elution buffers One of the following compositions is used as the elution buffer.

E1: Water (100%), pH 8.0

E2: 10 mmol/l Tris/HCl (pH 8.5), 0.1 mmol/l EDTA•2Na

E3: 50 mmol/l Tris/HCl (pH 8.5), 0.1 mmol/l EDTA•2Na 3.5 Enzymes

One of the following enzymes is used.

protease: Proteolytic enzyme proteinase K: Alkaline proteinase K

EXAMPLES

Example 1

Nucleic Acids Extraction from Whole Blood (The Second Method)

According to the second method illustrated in FIG. 3 and FIG. 5, nucleic acids are extracted from the human whole blood 1 (100 μL). In the lysis process, the whole blood 1 (100 μL) and a lysis buffer (100 μL) are added to a tube 5 containing proteinase K (6) (10 μL), followed by stirring into a mixed solution. The lysis buffer used here contains guanidine hydrochloride at a concentration of 3 M and Triton X-100 at 5% by volume. The mixed solution is incubated at 70° C. for 10 minutes. Thereafter, an additive solution (100 μL) selected from among EGDME, EGDEE, PGDME, PGDEE, DIGLYME, DGDEE, THF, DX, PGMEA, EL, HAC, AC, and MEK is added, and the resulted mixture is stirred.

In the adsorption process, the procedure for bi-directional transfer of the mixed solution by suction and discharge is repeated 10 times using a column 14 packed with an adsorption support 13 (product of Toshiba Ceramics Co., Ltd.).

In the washing process, the washing buffer (W1) 15 placed in another tube 16 undergoes the procedure for bi-directional transfer for three times.

In the elution process, an elution buffer 18 placed in a further tube 17 is sucked up to a level such that the adsorption support is wholly immersed in that buffer, and the buffer stands in that condition for 2 minutes. Thereafter, the elution buffer is removed by centrifugation. The nucleic acids are thus collected.

The nucleic acids solution obtained could be used in subsequent reactions, such as PCR, or analysis without any purification, such as precipitation.

Table 1 shows the nucleic acids yields obtained by using various additive solutions and the A260/A280 values indicative of the purities of the nucleic acids in the respective extracted nucleic acids solutions.

TABLE 1

| No. | Additive solution | Nucleic acids yield ($\mu$g) | A260/A280 |
| --- | --- | --- | --- |
| 1 | EGDME | 1.6 | 1.7 |
| 2 | EGDEE | 1.8 | 1.8 |
| 3 | PGDME | 1.5 | 1.7 |
| 4 | PGDEE | 1.4 | 1.8 |
| 5 | DIGLYME | 1.9 | 1.9 |
| 6 | DGDEE | 1.8 | 1.8 |
| 7 | THF | 1.5 | 1.7 |
| 8 | DX | 1.5 | 1.8 |
| 9 | PGMEA | 1.4 | 1.7 |
| 10 | EL | 2.0 | 1.9 |
| 11 | IIAC | 1.6 | 1.8 |
| 12 | AC | 1.5 | 1.7 |
| 13 | MEK | 1.3 | 1.7 |

In the above, A260 denotes the absorbance at the wavelength 260 nm of the nucleic acid-containing aqueous solution. When the A260/A280 value is 1.8, the nucleic acids concerned are regarded as being pure. An A260/A280 value within the range of 1.7 to 1.9 is regarded as being sufficiently pure. The same enzyme (proteinase K), lysis buffer, washing buffer, and elution buffer are used in the series of experiments, and the results are shown in Table 1. The nucleic acids obtained are quantified by fluorometry using the fluorescent dye PicoGreen (Molecular Probes Inc.) for quantifying double-stranded nucleic acids. For each additive solution, it appears that high-purity nucleic acids are obtained.

Figure 6:
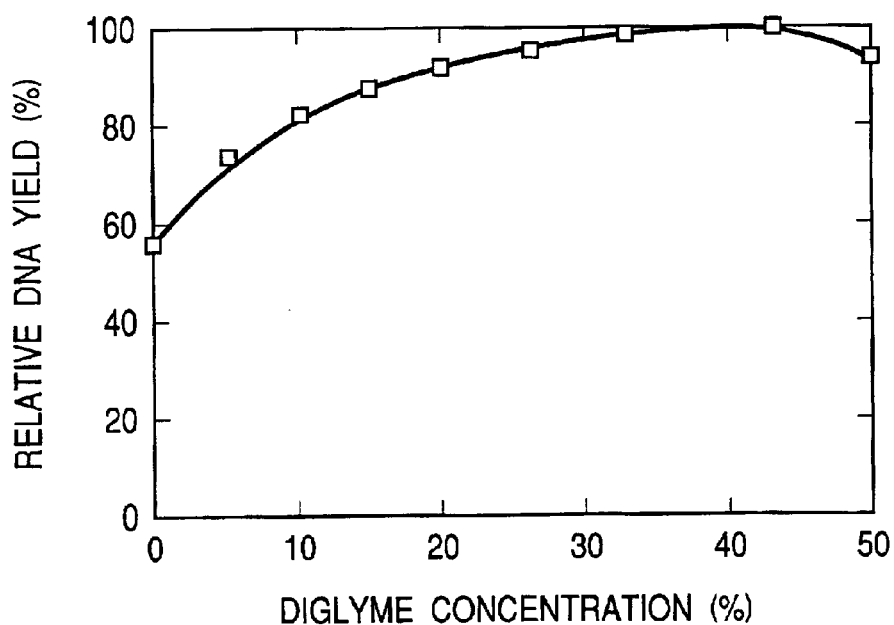
FIG. 6 shows the correlation between the Diglyme concentration in the mixed solution and the respective nucleic acids yield as found in some embodiments of the invention.

FIG. 6 shows the change in nucleic acids yield along with the concentration change of the additive solution of Diglyme. The abscissa denotes the Diglyme concentration (% by volume) in the mixed solution 7, and the ordinate denotes the relative yield (%) with the maximum yield taken as 100. The relative yield should not be lower than 80% (the desired yield). In the Diglyme concentration range of 5% to 50%, the relative yields are higher than 80%. In particular, it is seen that the maximum yield is obtained when the concentration is about 43%.

Figure 7:
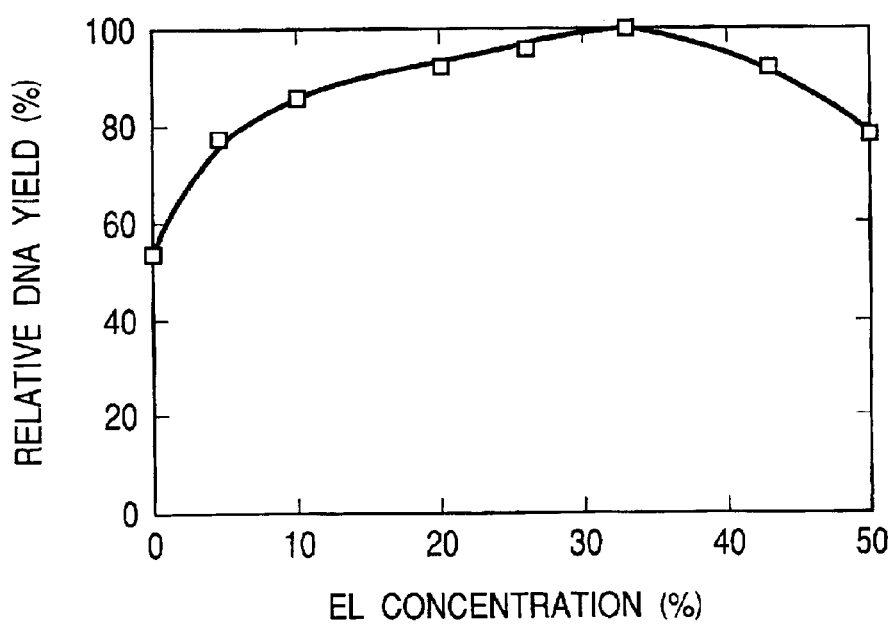
FIG. 7 shows the correlation between the EL concentration in the mixed solution and the respective nucleic acids yield as found in some embodiments of the invention.

FIG. 7 shows the change in nucleic acids yield along with the concentration change of the additive solution of EL. In the series of experiments, the same enzyme (proteinase K), lysis buffer, washing buffer, and elution buffer are used. When the relative yield is not lower than 80%, the desired yield is obtained. In the EL concentration range of 10% to 50%, the relative yields are higher than 80%. In particular, it is seen that the maximum yield is obtained when the addition level is about 33%.

Figure 8:
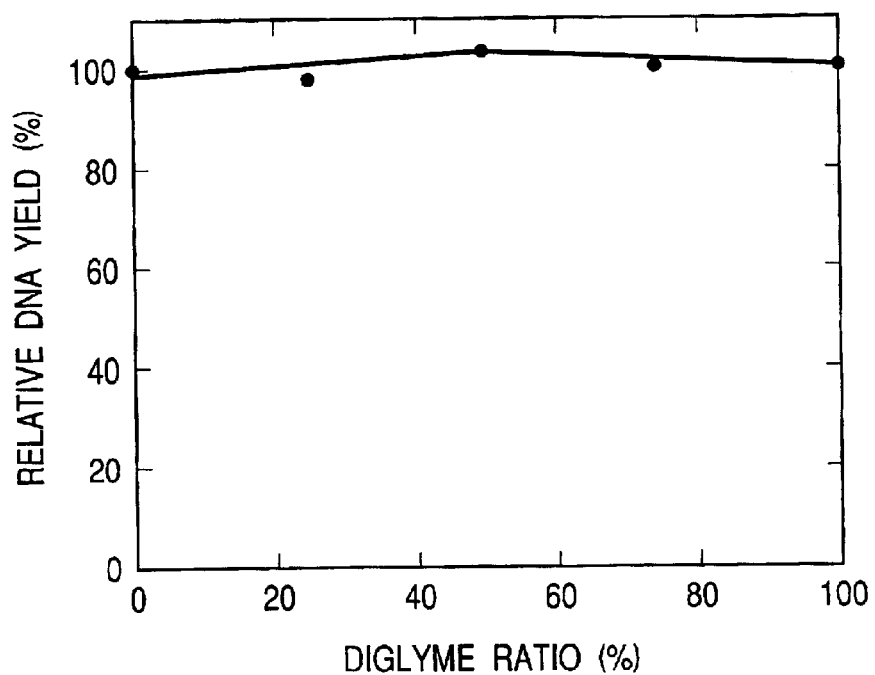
FIG. 8 shows the proportion of Diglyme in the additive solution comprising Diglyme and EL and the respective nucleic acids yield as found in some embodiments of the invention.

FIG. 8 shows the change in nucleic acids yield when Diglyme and EL are mixed as the additive solution. Here, the level of addition of the additive solution corresponds to 33% of the whole mixed solution. In FIG. 8, the abscissa denotes the proportion (by volume) of Diglyme in the additive solution. When the relative yield is not lower than 80%, the desired yield is obtained. It is seen that the desired yield can be obtained at any proportion of Diglyme.

Figure 9:
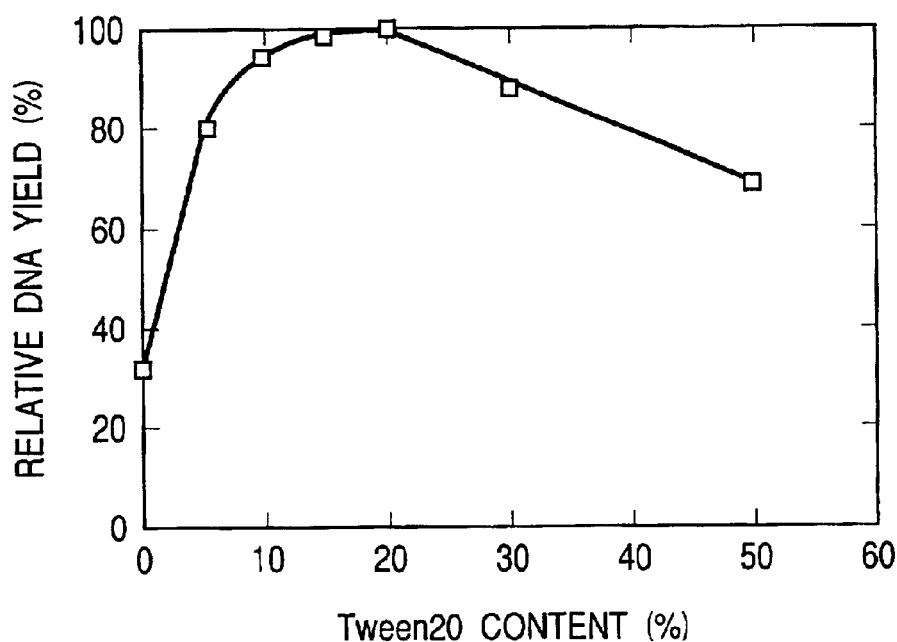
FIG. 9 shows the correlation between the content of Tween 20 in the lysis buffer and the respective nucleic acids yield as found in some embodiments of the invention.
Figure 10:
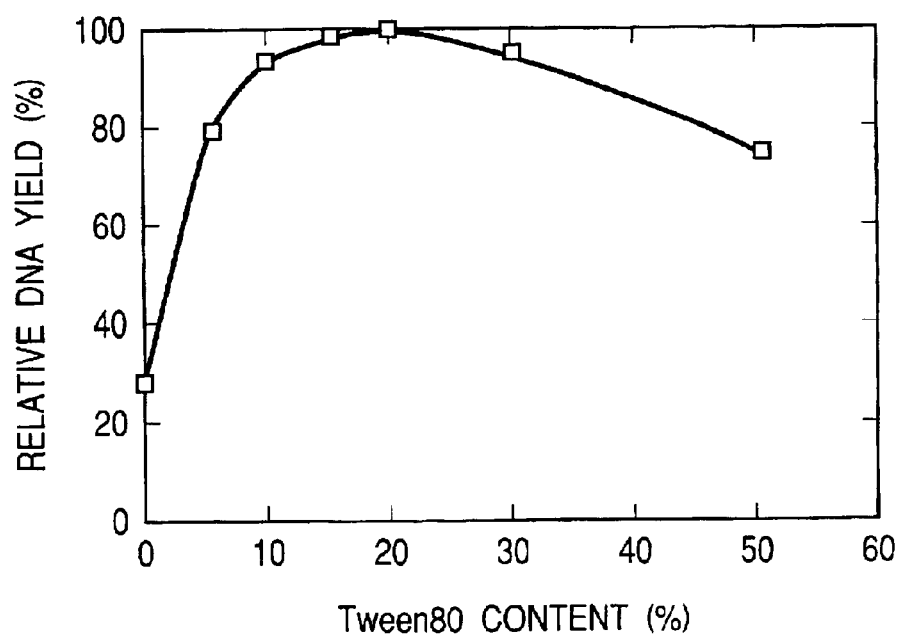
FIG. 10 shows the correlation between the content of Tween 80 and the respective nucleic acids yield as found in some embodiments of the invention.
Figure 11:
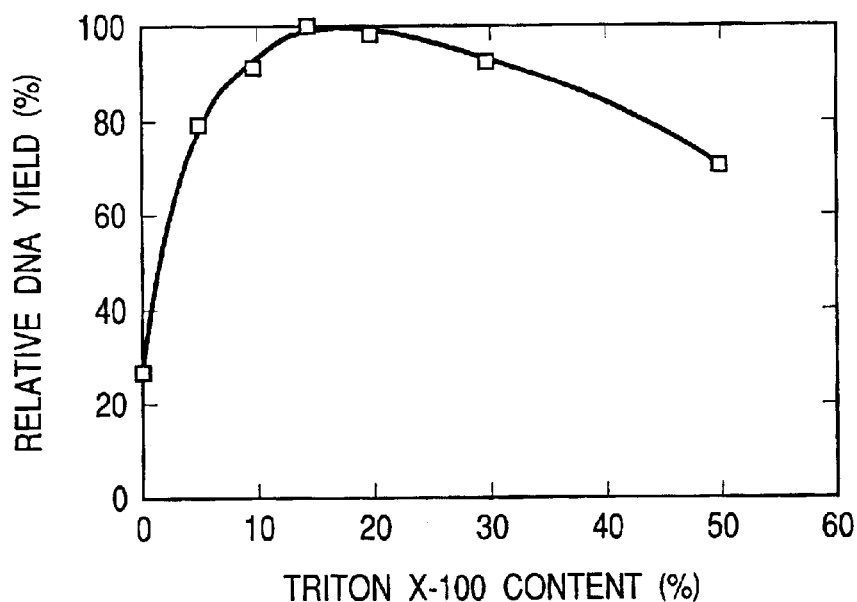
FIG. 11 shows the correlation between the content of Triton X-100 in the lysis buffer and the respective nucleic acids yield as found in some embodiments of the invention.

FIG. 9, FIG. 10, and FIG. 11 each shows the relation between the surfactant concentration in the lysis buffer and the nucleic acids yield. In the series of experiments, the results are shown in FIG. 9 to FIG. 11, while the same enzyme (proteinase K), additive solution, washing buffer, and elution buffer are used. When the relative yield is not lower than 80%, the desired yield is obtained. It is indicated that relative nucleic acids yields are higher than 80% when the surfactant content is 5% to 50%.

Figure 12:
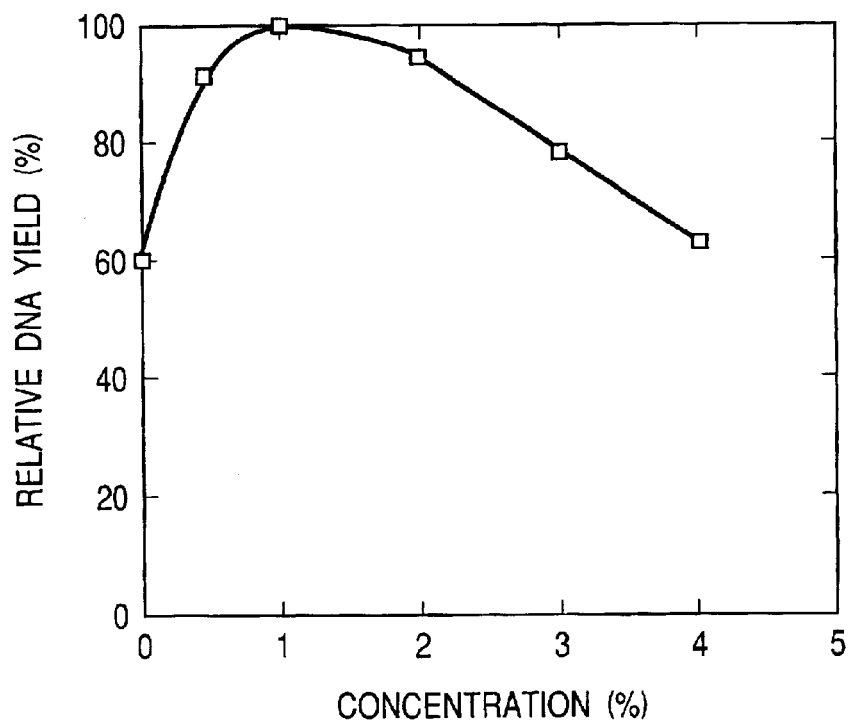
FIG. 12 shows the correlation between the level of addition of the defoaming agent CE-457 to the lysis buffer and the respective nucleic acids yield as found in some embodiments of the invention.

FIG. 12 shows the relation between the level of addition of a defoaming agent (CE-457) in the mixed solution 7 and the nucleic acids yield. In the series of experiments, the same enzyme (proteinase K), additive solution, washing buffer, and elution buffer are used. The lysis buffers have the same composition except for the concentration of the defoaming agent. It is indicated that the nucleic acids yields are higher than 80% within the defoaming agent addition level range of 0.2% to 2.5%. It is thus shown that the addition of a defoaming agent is effective not only in preventing the mixed solution from foaming but also in improving the nucleic acids yield.

Table 2 shows that the employment of Diglyme in the additive solution enhances the adsorption operability (Viscosity coefficient: Organic Solvents, Fourth Edition, John Wiley & Sons, Inc., 1986).

TABLE 2

| Additive solution | Viscosity coefficient at 25° C., $\eta$(kg m$^{-1}$ s$^{-1}$) | Time required for adsorption process (s) |
| --- | --- | --- |
| Ethanol | 1.0826 | 60 |
| Diglyme | 0.989 | 50 |

As compared with ethanol, namely a compound representative of the alcohols described in Tokuhyo No. 501321/1996, the additive solution Diglyme applied in the present invention is lower in viscosity and, therefore, the viscosity of the mixed solution in the adsorption process becomes lower, hence the resistance against passage thereof through the column 14 becomes lower, as evidenced by the result that the time required for adsorption process is shortened by 10 seconds. Foaming is also prevented, hence the degree of contamination decreased, and the adsorption operability improved.

Table 3 shows the flash points of various additive solutions (solvents). These solvents are examined for safety based on these data ("Yozai Pokettobukku (Solvent Pocketbook)", edited by the Society of Organic Synthetic Chemistry, Japan, published by Ohmsha, Ltd.).

TABLE 3

| Additive solution | Flash point (° C.) |
| --- | --- |
| Ethanol | 13 |
| Diglyme | 56 |
| EL | 52 |
| EGDEE | 35 |
| DGDEE | 82 |
| EGDME | -2 |
| THF | -14 |
| DX | 12 |
| AC | -15 |
| MEK | -7 |

Flash point comparison reveals that the flash points of Diglyme, EL, EGDEE, and DGDEE are higher than the flash point of ethanol. Therefore, the use of Diglyme, EL, EGDEE, and DGDEE, among others, as additive solutions is less dangerous from the viewpoint of explosion and fire, among other, hence preferred from the safety viewpoint.

Example 2

Nucleic Acids Extraction from Whole Blood (The Second Method)

Nucleic acids are extracted from human whole blood 1 (1 mL) according to the second method depicted in FIG. 3 and FIG. 5. In the lysis process, the whole blood 1 (1 mL) and a lysis buffer (1 mL) are added to a tube 5 containing proteinase K (6) (100 μL), followed by stirring into a mixed solution. The lysis buffer used here contained a concentration of 3 M of guanidine hydrochloride and Triton X-100 at 5% by volume. The mixed solution is incubated at 70° C. for 10 minutes. Thereafter, an additive solution (1 mL) selected from Diglyme and ethanol is added, and the mixture is stirred.

In the adsorption process, the procedure for bi-directional transfer of the mixed solution 7 is repeated 10 times using a column 14 packed with an adsorption support 13 (100 mg) (product of Tosoh Quartz Corp.).

In the washing process, the washing buffer 15 (W1) (3 mL) placed in another tube 16 undergoes the suction/discharge operation for bi-directional transfer for three times.

In the elution process, an elution buffer 18 (1 mL) placed in a further tube 17 is sucked up to a level such that the adsorption support 13 is wholly immersed in the buffer. The buffer stands in that state for 2 minutes. Thereafter, the elution buffer 18 is discharged into the tube 17. A nucleic acids solution is thus recovered.

The nucleic acids solution obtained could be used in subsequent reactions and analysis, for example PCR, without any further purification, such as precipitation.

Table 4 shows the nucleic acids yields and the A260/A280 values for the nucleic acids solutions obtained when ethanol and Diglyme are respectively used as additive solutions.

TABLE 4

| Additive solution | Nucleic acids yield (μg) | A260/A280 |
| --- | --- | --- |
| Diglyme | 15.0 | 1.8 |
| Ethanol | 0.6 | 1.8 |

While when ethanol is used as the additive solution, the nucleic acids yield is 0.6 μg, the use of Diglyme gives 15.0 μg. Therefore, Diglyme is superior additive to the additive solution than Ethanol.

Example 3

Nucleic Acids Extraction from Whole Blood (The First Method)

Nucleic acids are extracted from 100 μL of human whole blood according to the first method illustrated in FIG. 3 and FIG. 4.

The lysis process is carried out in the same manner as in Example 1. The same enzyme, lysis buffer, additive solution, washing buffer, and elution buffer as in Example 1 are used.

In the adsorption process, the mixed solution is poured into a spin column 8 and centrifuged (number of revolutions 6,000 rpm) for 1 minute using a desk centrifuge (number of revolutions 6,000 rpm).

In the washing process, a washing buffer (W2) 11 (500 μL) is poured into the spin column 8, and centrifugation is conducted for 1 minute (number of revolutions 6,000 rpm).

In the elution process, an elution buffer (E2) 12 (100 μL) is poured into the spin column 8. After standing for 2 minutes at room temperature (25° C.), the nucleic acids are collected by 1 minute of centrifugation (number of revolutions 6,000 rpm). The nucleic acids are quantified, and the purity of the nucleic acids is evaluated.

In this method, the same results as in Example 1 are obtained.

Example 4

Nucleic Acids Extraction from Tissue (The First Method)

Rat liver tissues (25 mg) are mixed with 80 μL of PBS (phosphate buffered saline) and mechanically homogenized. Protease K (20 μL) is added, and the mixture is stirred and heated at 56° C. until the tissue is dissolved. A lysis buffer (200 μL) containing a concentration of 3 M of guanidine hydrochloride and Tween 80 at 5% by volume is added, and the resulted mixed solution is stirred and heated at 70° C. for 10 minutes. Diglyme (200 μL) is added, followed by stirring. The above steps constituted the lysis process.

In the adsorption process, the mixed solution is poured into a spin column 8 and centrifuged (number of revolutions 6,000 rpm) for 1 minute using a desk centrifuge.

In the washing process, a washing buffer (W3) 11 (500 μL) is poured into the spin column 8, and centrifugation is carried out for 1 minute (number of revolutions 6,000 rpm).

In the elution process, an elution buffer 12 (100 μL) selected from the above-mentioned E1, E2 and E3 is poured into the spin column 8. After standing for 2 minutes at room temperature (25° C.), the nucleic acids are recovered by 1 minute of centrifugation (number of revolutions 6,000 rpm) such that they are quantified, and the purity of the nucleic acids is evaluated.

As a result, high-purity nucleic acids with an A260/A280 ratio of 1.8 are obtained, and they could be used in the PCR.

Example 5

Nucleic Acids Extraction from Tissue (The First Method)

Nucleic acids are extracted from 20 mg of bladder tissues (rat) in the same manner as in Example 4. As a result, highly pure nucleic acids with an A260/A280 ratio of 1.7 are obtained. They could be used in the PCR.

Example 6

Nucleic Acids Extraction from Urine (The First Method)

A urine sample (20 mL) is centrifuged (number of revolutions 14,000 rpm) for 5 minutes. The supernatant is removed, and the urine sediments are separated. The urine sediments is added with 200 μL of a regent solution containing a concentration of 3 M of guanidine hydrochloride and Triton X-100 at 5% by volume. After stirring, the mixture is heated at 70° C. for 10 minutes. Diglyme (200 μL) is added, followed by stirring. The above steps constituted the lysis process.

In the adsorption process, the mixed solution is poured into a spin column 8 and centrifuged (number of revolutions 6,000 rpm) for 1 minute using a desk centrifuge.

In the washing process, a washing buffer (W4) 11 (500 μL) is poured into the spin column 8, and centrifugation (number of revolutions 6,000 rpm) is effected for 1 minute.

In the elution process, an elution buffer (E3) 12 (100 μL) is poured into the spin column 8. After standing for 2 minutes at room temperature (25° C.), the nucleic acids are collected by 1 minute of centrifugation such that they are quantified, and the impurity of the nucleic acids is evaluated.

As a result, high-purity nucleic acids with an A260/A280 ratio of 1.8 are obtained, and they could be used in the PCR.

Example 7

Nucleic Acids Extraction from Cells (The First Method)

$10^6$ HeLa cells are dispersed in PBS (100 μL), 200 μL of a lysis buffer containing a concentration of 3 M of guanidine hydrochloride and Triton X-100 at 5% by weight is added, and the mixture is stirred and heated at 70° C. for 10 minutes. Diglyme (200 µL) is added, followed by stirring. The above steps constituted the lysis process.

In the adsorption process, the mixed solution is poured into a spin column 8 and centrifuged (number of revolutions 6,000 rpm) for 1 minute using a desk centrifuge.

In the washing process, a washing buffer (W2) 11 (500 µL) is poured into the spin column 8, and centrifugation (number of revolutions 6,000 rpm) is carried out for 1 minute.

In the elution process, an elution buffer (E1) 12 (100 µL) is poured into the spin column 8. After standing for 2 minutes at room temperature (25° C.), the nucleic acids are collected by 1 minute of centrifugation (number of revolutions 6,000 rpm). The nucleic acids recovered are quantified, and the purity of the nucleic acids is evaluated.

As a result, highly pure nucleic acids with an A260/A280 ratio of 1.8 are obtained. They could be used in the PCR.

The invention provides a method for isolating and purifying nucleic acids with a high recovery yield and shorter time. It thus is excellent in operability and less susceptible to contamination.

The foregoing invention has been described in terms of preferred embodiments. However, those skilled in the art will recognize that many variations of such embodiments exist. Such variations are intended to be within the scope of the present invention and the appended claims.

What is claimed is:

1. A method for isolating and purifying nucleic acids, which comprises:

providing a mixed solution containing the nucleic acids, salts, and at least one organic solvent;

adsorbing the nucleic acids on an adsorption support;

washing the support adsorbed with the nucleic acids with a washing buffer;

desorbing the nucleic acids from the support with an elution buffer thereby recovering the nucleic acids, wherein said organic solvent includes at least one of ethylene glycol dimethyl ether, ethylene glycol diethyl ether, propylene glycol dimethyl ether, propylene glycol diethyl ether, diethylene glycol dimethyl ether, diethylene glycol diethyl ether, tetrahydrofuran, 1,4-dioxane, propylene glycol monomethyl ether acetate, ethyl lactate, hydroxyacetone, acetone, and methyl ethyl ketone.

2. The method for isolating and purifying nucleic acids as claimed in claim 1, wherein the concentration of the organic solvent in said mixed solution is not more than 50% by volume.

3. The method for isolating and purifying nucleic acids as claimed in claim 2, wherein the concentration of the organic solvents in said mixed solution is 5% to 50% by volume.

4. The method for isolating and purifying nucleic acids as claimed in claim 1, wherein said mixed solution contains a surfactant at no more than 50% by volume.

5. The method for isolating and purifying nucleic acids as claimed in claim 4, wherein said mixed solution contains a surfactant at 5% to 50% by volume.

6. The method for isolating and purifying nucleic acids as claimed in claim 1, wherein said mixed solution contains a defoaming agent at 0.2% to 2.5% by volume.

7. The method for isolating and purifying nucleic acids as claimed in claim 1, further comprises:

providing a column with a bottom;

placing the support above the bottom;

causing the mixed solution to pass one-way through the support to the bottom by a sucking force.

8. The method for isolating and purifying nucleic acids as claimed in claim 7, whereby the causing step, the mixed solution also passes through the support the other way by an opposite sucking force.

9. The method for isolating and purifying nucleic acids as claimed in claim 8, whereby the causing step, the mixed solution passes through the support a number of times to enhance adsorption efficiency.

* * * * *